United States Patent
Qu et al.

(10) Patent No.: US 8,204,289 B2
(45) Date of Patent: Jun. 19, 2012

(54) SYSTEM FOR IDENTIFYING MEDICAL IMAGES HAVING A PARTICULAR MEDICAL CHARACTERISTIC

(75) Inventors: Wei Qu, Schaumburg, IL (US); Yuanyuan Jia, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 702 days.

(21) Appl. No.: 12/355,980

(22) Filed: Jan. 19, 2009

(65) Prior Publication Data

US 2009/0279765 A1 Nov. 12, 2009

Related U.S. Application Data

(60) Provisional application No. 61/051,768, filed on May 9, 2008.

(51) Int. Cl.
*G06K 9/00* (2006.01)
(52) U.S. Cl. ......... 382/130; 382/132; 600/420; 600/431
(58) Field of Classification Search .................. 382/130, 382/132; 600/420, 431
See application file for complete search history.

(56) References Cited

U.S. PATENT DOCUMENTS

| 2005/0234355 A1* | 10/2005 | Rowlandson | 600/509 |
|---|---|---|---|
| 2008/0119715 A1* | 5/2008 | Molezzi et al. | 600/407 |
| 2008/0144126 A1* | 6/2008 | Kanakubo | 358/468 |
| 2009/0005831 A1* | 1/2009 | Wilson et al. | 607/27 |

OTHER PUBLICATIONS

Co-pending U.S. Appl. No. 12/026,145, filed Feb. 5, 2008, Qu, et al.
Bhargava, V., Hagan, G., Miyamoto, M.I., Ono, S., Ono, S., Rockman, H., Ross, J., Jr: Systolic and diastolic global right and left ventricular function assessment in small animals using an automated angiographic technique. In: Proceedings of Computers in Cardiology. (2002) 191-1942.
Sandler, H., Dodge, H.T.: The use of single plane angiocardiograms for the calculation of left ventricular volume in man. Amer. Heart J. 75(3) (1968) 325-334.
Qu, W., Singh, S., Keller, M.: AutoEDES: A model-based Bayesian framework for automatic end-diastolic and end-systolic frame selection in angiographic image sequence. In: Proc. SPIE International Conf. on Medical Imaging. (2008).
Rabiner, L.R., Juang, B.H.: An introduction to hidden Markov models. IEEE ASSP Mag. (Jan. 1986) 4-155.
Arzeno, N. M., Poon, C.S., Deng, Z.D.: Quantitative analysis of QRS detection algorithms based on the first derivative of the ecg. In: Proc. IEEE Conf. Eng Med Biol Soc. (2006) 1788-1791.
Arzeno, N., Deng, Z., Poon, C.: Analysis of first-derivative based QRS detection algorithms. IEEE Trans Biomed Eng. 55(2) (2008) 478-484.

* cited by examiner

*Primary Examiner* — Arnold Kinkead
*Assistant Examiner* — Richard Tan
(74) *Attorney, Agent, or Firm* — Alexander J Burke (57) ABSTRACT

A system identifies a particular image associated with a particular cardiac characteristic from within a sequence of cardiac images including image noise artifacts and obtained over a heart beat cycle. The system comprises at least one repository including, first data comprising heart cycle information derived from ECG data, second data comprising data representing multiple images acquired over at least one heart cycle and third data comprising data associated with timing of contrast agent flow. An image data processor identifies a particular image exhibiting a particular cardiac characteristic from within a sequence of cardiac images by processing the first, second and third data to identify an image having a substantially maximum likelihood of exhibiting the particular cardiac characteristic. A storage processor retrieves data representing the particular image from storage.

11 Claims, 6 Drawing Sheets

| METHOD | SYSTEM 10 | OTHER SYST. |
|---|---|---|
| ED ACCURACY | 99% | 86% |
| ES ACCURACY | 95% | 72% |
| EXTRA-SYSTOLIC | GOOD | NONE |
| LOW FRAME RATE | GOOD | OK |
| BACKGROUND MOTION | GOOD | OK |
| LIGHTNESS CHANGE | GOOD | POOR |
| POOR DYE CONTRAST | GOOD | POOR |
| SMALL ES LV | GOOD | POOR |

FIG. 6a

| SPEED OF DIFFERENT MODULES | | | | OTHER SYST. SPEED |
|---|---|---|---|---|
| HISTOGRAM MODEL | SCENE MODEL | ECG PROCESSING | DATA FUSION | |
| 143 MILLISECONDS | 156 MILLISECONDS | 23 MILLISECONDS | 18 MILLISECONDS | 302 MILLISECONDS |

SYSTEM FOR IDENTIFYING MEDICAL IMAGES HAVING A PARTICULAR MEDICAL CHARACTERISTIC

This is a non-provisional application of provisional application Ser. No. 61/051,768 filed May 9, 2008, by W. Qu et al.

FIELD OF THE INVENTION

This invention concerns a system for identifying a particular image associated with a particular characteristic from within a sequence of images such as cardiac images including image noise artifacts and obtained over a heart beat cycle, for example.

BACKGROUND OF THE INVENTION

Left ventricular angiography is widely used to evaluate clinical cardiac functions such as ejection fraction, stroke volume, and wall motion abnormalities. During imaging examination, X-ray opaque contrast dye is injected into a patient left ventricle in order to visualize its variation. Medical imaging systems are typically used to capture an X-ray image sequence covering 5 to 10 cardiac cycles. In order to analyze the clinical parameters, an end-diastolic (ED) image where the left ventricle is fully filled and an end-systolic (ES) image where the ventricle is maximally contracted are retrieved from the image sequence. Image analysis such as boundary identification (contour segmentation) is performed to determine ventricular volume. Since ED and ES image retrieval is involved in analyzing cardiac functions, accurate image selection is desirable for subsequent image analysis. In known clinical work flow, ED and ES images are typically manually selected as the image frames that have the largest and smallest opacified left ventricular area, respectively. There are often hundreds of images in each left ventricular angiogram which makes manual selection of the ED and ES images burdensome, time consuming and vulnerable to human error.

Automated, intelligent and accurate ED and ES image identification and retrieval may substantially reduce user burden and increase analysis accuracy. However, automated ED and ES image identification is difficult because of low contrast and noisy background in X-ray left ventricular images and because of the wide variation and dynamic change in left ventricular shape. A system according to invention principles addresses these deficiencies and related problems.

SUMMARY OF THE INVENTION

A system combines different types of information for use in identifying and retrieving ED and ES images from left ventricular image sequences. A system identifies a particular image associated with a particular cardiac characteristic from within a sequence of cardiac images including image noise artifacts and obtained over a heart beat cycle. The system comprises at least one repository including, first data comprising heart cycle information derived from ECG data, second data comprising data representing multiple images acquired over at least one heart cycle and third data comprising data associated with timing of contrast agent flow. An image data processor identifies a particular image exhibiting a particular cardiac characteristic from within a sequence of cardiac images by processing the first, second and third data to identify an image having a substantially maximum likelihood of exhibiting the particular cardiac characteristic. A storage processor retrieves data representing the particular image from storage.

DETAILED DESCRIPTION OF THE INVENTION

The operation of known systems for automatic ED (end-diastolic) and ES (end-systolic) image frame selection in an angiographic image sequence is impaired if the angiographic images are of poor image quality and the known systems fail to accommodate extra-systolic artifacts. A system according to invention principles combines different types of information for use in automatically identifying and retrieving ED and ES images from left ventricular image sequences in real time. The system integrates different kinds of information including heart cycle information derived from ECG data as well as data comprising multiple images acquired over at least one heart cycle and data associated with timing of contrast agent flow, in order to optimally estimate ED and ES image frames in a sequence.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

Figure 1:
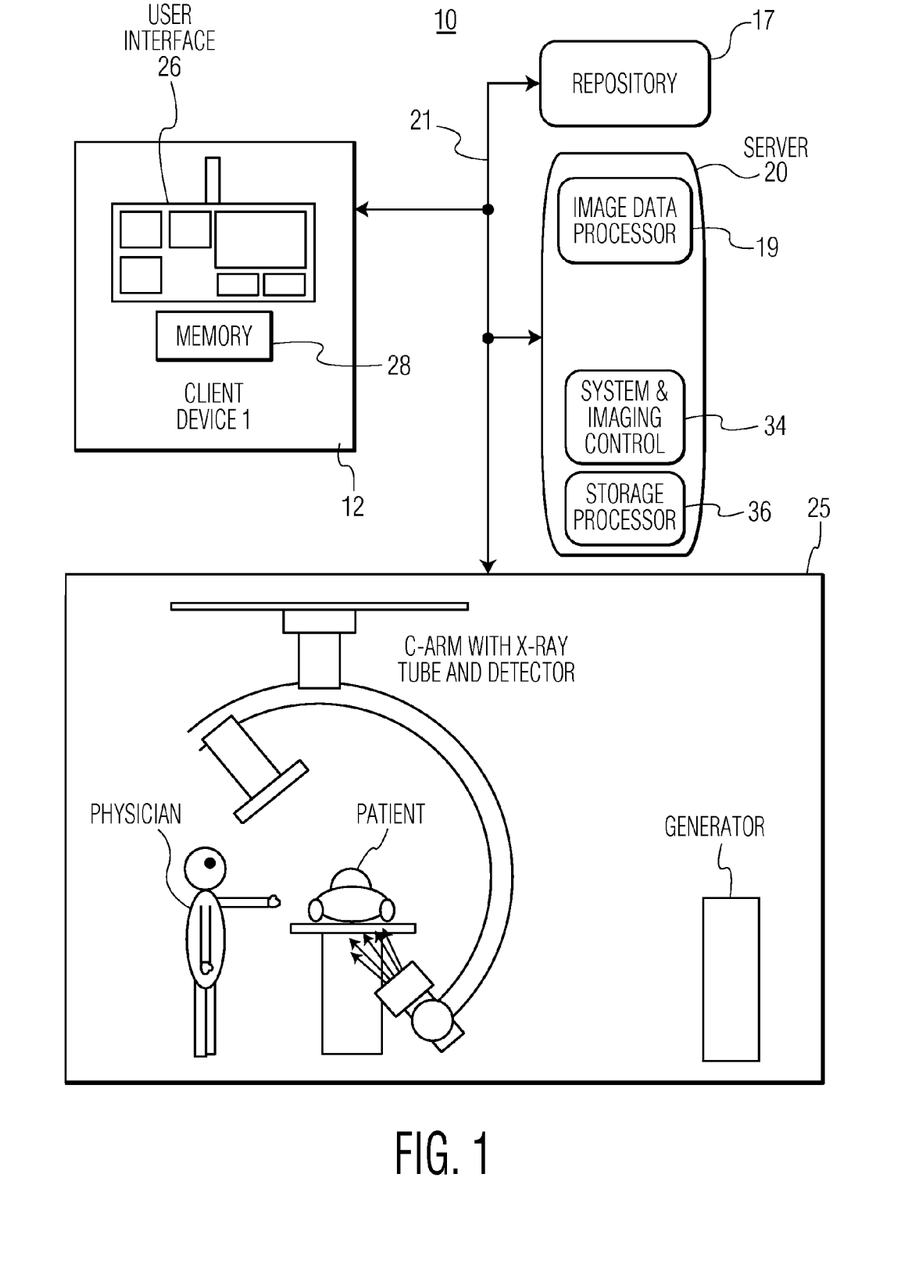
FIG. 1 shows an X-ray imaging system including a system for identifying a particular image associated with a particular cardiac characteristic, according to invention principles.

FIG. 1 shows X-ray imaging system 10 including a system for identifying a particular image associated with a particular cardiac characteristic within a sequence of cardiac images including image noise artifacts and obtained over a heart beat cycle. System 10 includes one or more processing devices (e.g., workstation or portable devices such as notebooks, Personal Digital Assistants, phones) 12 that individually include memory 28 and a user interface 26 supporting image presentation in response to user command and predetermined user (e.g., physician) specific preferences. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. User interface 26 provides data representing display images comprising a Graphical User Interface (GUI) for presentation on workstation 12. At least one repository 17 includes, first data comprising heart cycle information derived from ECG data, second data comprising data representing multiple images acquired over at least one heart cycle and third data comprising data associated with timing of contrast agent flow. At least one repository 17 also includes medical image studies for multiple patients in DICOM compatible (or other) data format. A medical image study individually includes multiple image series of a patient anatomical portion which in turn individually include multiple images. Server 20 includes image data processor 19, storage processor 36 and system and imaging controller 34.

Image data processor 19 identifies a particular image exhibiting a particular cardiac characteristic from within a sequence of cardiac images by processing the first, second and third data to identify an image having a substantially maximum likelihood of exhibiting the particular cardiac characteristic. Storage processor 36 retrieves data representing the particular image from storage. System 10 acquires data representing multiple temporally sequential individual images of a patient organ (e.g., a heart) using X-ray modality system 25. X-ray modality system 25 comprises a C-arm X-ray radiation source and detector device rotating about a patient table and an associated electrical generator for providing electrical power for the X-ray radiation system.

Figure 2:
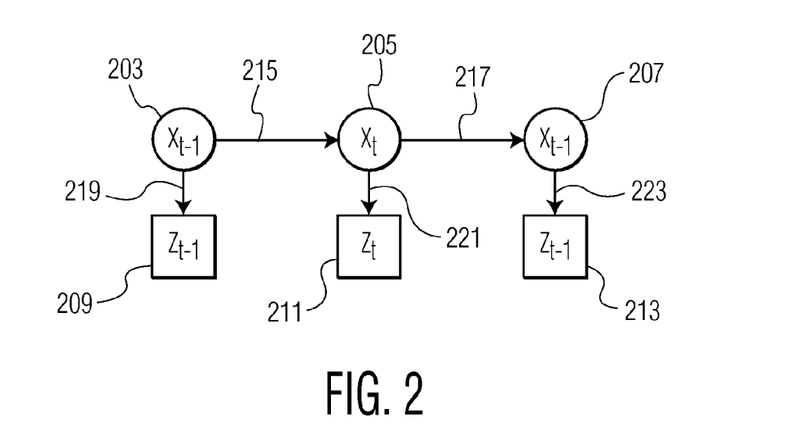
FIG. 2 illustrates modeling of a left ventricular angiogram sequence using a Hidden Markov Model (HMM).

FIG. 2 illustrates modeling of a left ventricular angiogram sequence using a Hidden Markov Model (HMM). Circle nodes 203, 205 and 207 indicate states representing an area value of a left ventricle at different times indicated by time index t. Square nodes 209, 211 and 213 represent image features corresponding to states 203, 205 and 207 respectively. The directional links 215 and 217 between consecutive states represent dynamic change $p(x_t|x_{t-1})$. It is a Markov chain where each state conditionally depends on a previous state. Directional links 219, 221 and 223 between states and its image features is a local likelihood density $p(z_t|x_t)$. A Bayesian propagation rule is derived based on the Markov model, $$p(x_{1:t}|z_{1:t}) = \frac{p(x_t, z_t|x_{1:t-1}, z_{1:t-1})}{p(z_{1:t})} p(x_{1:t-1}, z_{1:t-1}) \quad (1)$$

$$= \frac{p(x_t, z_t|x_{t-1})}{p(z_t)} p(x_{1:t-1}, z_{1:t-1}) \quad (2)$$

$$= \frac{p(z_t|x_t, x_{t-1})p(x_t|x_{t-1})}{p(z_t)} p(x_{1:t-1}, z_{1:t-1}) \quad (3)$$

$$\propto p(z_t|x_t, x_{t-1})p(x_t|x_{t-1})p(x_{1:t-1}, z_{1:t-1}) \quad (4)$$

where $p(z_t|x_t)$ is the local likelihood density, $p(x_t|x_{t-1})$ is the state transition, $p(x_{1:t-1}|z_{1:t-1})$ is a posterior density at time t−1. In equations (2) and (4), Markov properties are applied. The update equation recursively estimates a posterior density of state xt 205. Since a left ventricle changes its shape continuously and smoothly between consecutive image frames, the dynamics $p(x_t|x_{t-1})$ may be represented by a Gaussian distribution $N(0, \sigma_d)$, where $\sigma_d$ is a variance. The system employs effective feature extraction to estimate image feature information $z_t$ in observation likelihood $p(z_t|x_t)$ in equation (4). The feature extraction function of the system employs image data processing observation likelihood models including a histogram-based observation likelihood model and a scene-based observation likelihood model.

The histogram-based observation likelihood model takes advantage of the fact that in the beginning of a left ventricular angiogram, contrast agent is absent in a patient and image background does not change significantly enabling image background information to be determined. The histogram-based observation likelihood model accommodates background motion and other kinds of image noise. A number of images, say, $n_{BG}$, are selected from the beginning of a left ventricular angiogram sequence. The number selected is proportional to the total number of image frames in an angiogram sequence and also the frame rate to maximize inclusion of background information. The system selects a predefined region of interest (ROI) with size of $w_h$ by $h_h$ in individual image frames and generates a histogram based on the selected region of interest. In addition, the system may select a whole image as the ROI for simplicity. A histogram template $h_0$ is calculated by averaging the $n_{BG}$ histograms. This histogram represents an average pixel intensity distribution of an image background without contrast agent. The system generates a histogram for a ROI for individual images of an angiogram sequence and uses template histogram $h_0$ to calculate a local observation likelihood as follows:

$$p(z_t^h | x_t) = \frac{1}{k_h} \exp\left\{ -\frac{\left(x_t - \int \text{sign}(h_t^i - h_0^i)\right)^2}{2\sigma_h^2} \right\} \quad (5)$$

where $$\text{sign}(\cdot) = \begin{cases} 1 & \text{if}(h_t^i - h_0^i) > 0; \\ 0 & \text{otherwise} \end{cases} \quad (6)$$

i is the index of the histogram bins, $\sigma_h$ is a variance constant, and $k_h$ is a normalization factor. The histogram-based observation likelihood advantageously captures a global pixel intensity variation and accommodates background noise because the histogram is independent of pixel spatial information. However, the inventors have determined that the histogram-based likelihood model suffers from global lightness variation and has difficulty in accurately capturing a small region change especially during a cardiac ES phase where contrast agent area is relatively small. The histogram-based likelihood model may also fail to capture change in left ventricular area at all.

System 10 employs a scene-based observation likelihood model to improve analysis of image data. Specifically, system 10 selects a number of $M_{BG}$ images in the beginning of an angiogram sequence. This number can be same or different as $n_{BG}$. A substantially smaller window of size of $w_s$ by $h_s$ instead of the histogram-based likelihood model ROI, where $w_s < w_h$, and $h_s < h_h$, is automatically selected by system 10 for $M_{BG}$ images and advantageously reduces computation. The reduced size window encompasses a left ventricle region. In one embodiment, system 10 assumes the left ventricle resides in the middle of a scene. For individual pixels in the window, system 10 generates a background template $r_0$ by selecting a minimal intensity value from among $M_{BG}$ image candidates. The generated template comprises the blackest value of individual pixels occurring during the beginning of a left ventricular angiogram image sequence. System 10 performs background subtraction within the image window for each image frame, $r_t - r_0$, where $r_t$ is the image window at time t and calculates a scene-based observation likelihood as follows, $$p(z_t^s | x_t) = \frac{1}{k_s} \exp\left\{ -\frac{\left(x_t - \int_j \text{sign}(r_t^j - r_0^j)\right)^2}{2\sigma_s^2} \right\} \quad (7)$$

where $$\text{sign}(\cdot) = \begin{cases} 1 & \text{if}(r_t^j - r_0^j) > 0; \\ 0 & \text{otherwise} \end{cases} \quad (8)$$

j is the pixel index within the selected window, $\sigma_s$ the variance constant, $k_s$ is a normalization factor.

The image data processing histogram-based observation likelihood model and scene-based observation likelihood model are integrated by calculating a joint posterior density, $$p(x_{1:t} | z_{1:t}^h, z_{1:t}^s) \propto p(z_t^h, z_t^s | x_t) p(x_t | x_{t-1})$$
$$p(x_{1:t-1} | z_{1:t-1}^h, z_{1:t-1}^s) \quad (9)$$

$$= p(z_t^h | x_t) p(z_t^s | x_t) p(x_t | x_{t-1}) p(x_{1:t-1} | z_{1:t-1}^h, z_{1:t-1}^s) \quad (10)$$

assuming that the two observation likelihoods are conditionally independent.

ECG signals are typically recorded during left ventricular angiography and ECG signal data is independent of image data quality and contrast agent contrast. Further, an R-wave of an ECG signal corresponds to the ED phase of a cardiac cycle and a T-wave corresponds to the ES phase, therefore system 10 uses an ECG signal in ED and ES image selection. Unfortunately, inherent characteristics of an ECG signal impair operation of ECG QRS-complex detection functions in identifying ED and ES images. Specifically, (1) an ECG signal cannot indicate when a contrast agent is injected into a left ventricle and so an ECG signal cannot identify a particular cardiac cycle exhibiting optimum image contrast due to a contrast agent, (2) ECG QRS-complex detection functions generate both false positive and false negative results; (3) an ECG signal may have synchronization errors and (4) a T-wave is difficult to detect accurately because it is relative small and noise sensitive. In one embodiment, system 10 restricts ECG signal use in generating ED candidate images to use of R-wave detection.

Figure 3:
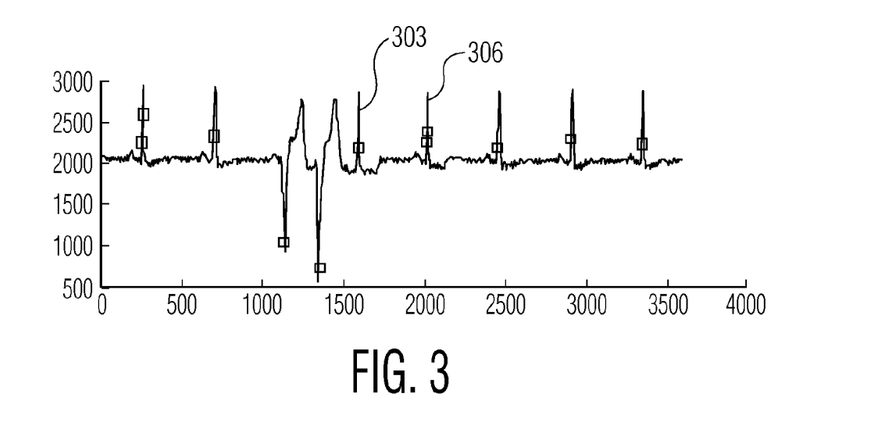
FIG. 3 illustrates R-wave detection in an ECG signal.

FIG. 3 illustrates detected R-waves (e.g., 303, 306) in an ECG signal identified using a first-derivative based algorithm. ED candidate images corresponding to detected R-waves in an ECG signal in an ED distribution density of an ECG signal are represented as a Gaussian mixture, $$f(t) = \sum_l N(t_l, \sigma_e) \quad (11)$$

where l is the index of ED candidates, σe is a variance constant.

System 10 employs prior domain knowledge in identification and retrieval of optimal ED and ES images. For example, extra-systolic phenomenon usually occur after a contrast agent is injected into a left ventricle, where a cardiac cycle in this period has an additional ES phase and the ED phase is also 20% to 25% bigger than usual. System 10 advantageously excludes ED and ES images corresponding to the extra-systolic phenomenon from identification and retrieval even though such images have good image contrast. Moreover, at the end of a left ventricular angiogram, contrast agent fades away and image quality of a left ventricle area is low. In order to provide images with good contrast agent enhanced image contrast for analysis, system 10 excludes images at the end of an angiogram sequence.

Figure 4:
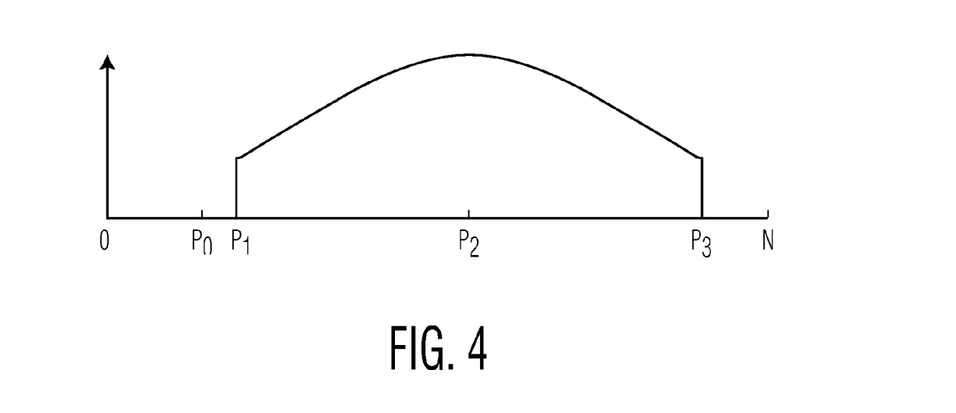
FIG. 4 illustrates a probability density function plotted against frame number N of a left ventricular angiogram, according to invention principles.
Figure 5A:
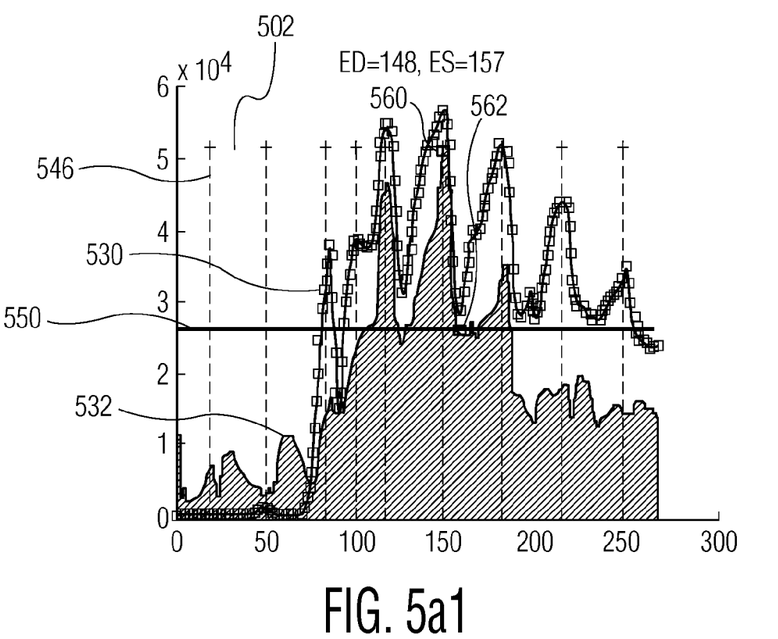
FIG. 5 shows data analysis graphs and associated corresponding ED and ES images, according to invention principles.
Figure 5A:
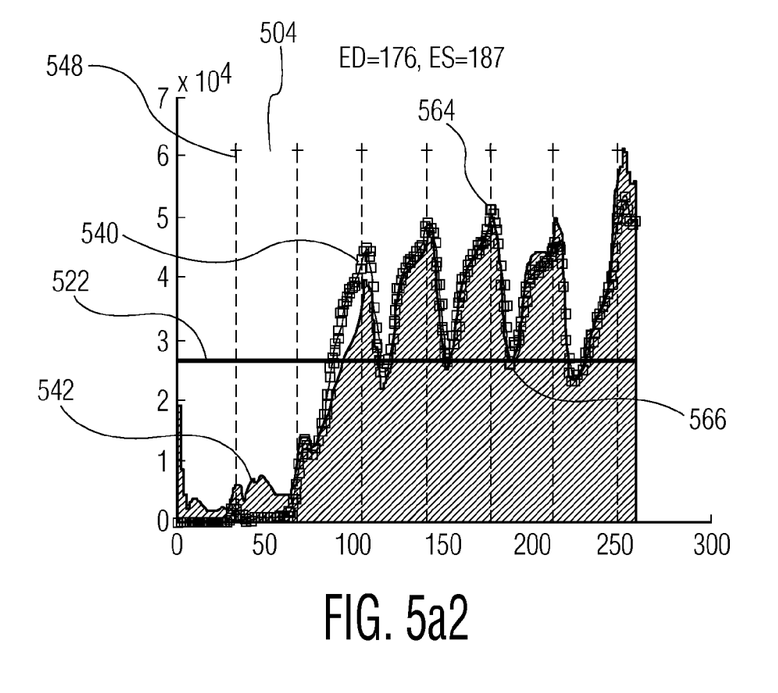
Figure 5B:
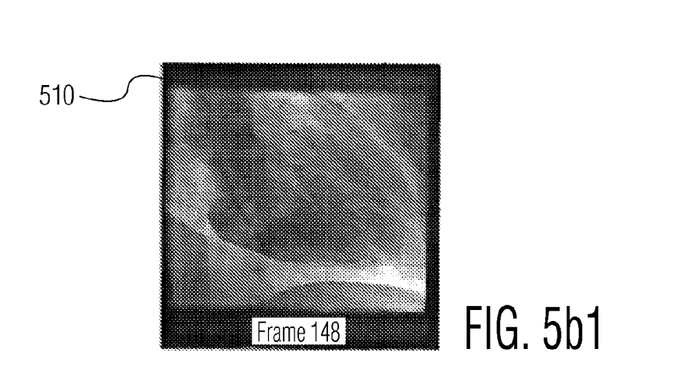
Figure 5B:
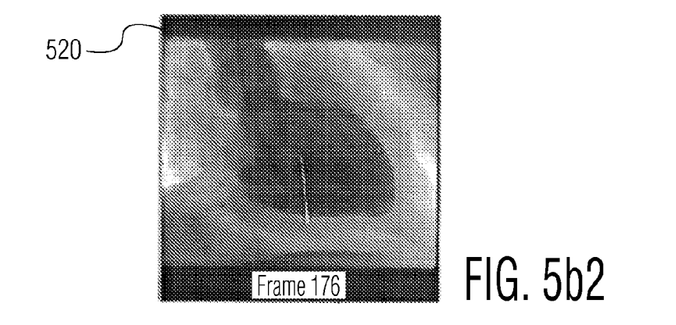
Figure 5C:
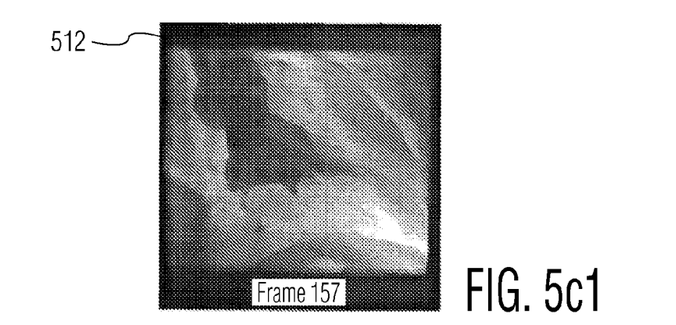
Figure 5C:
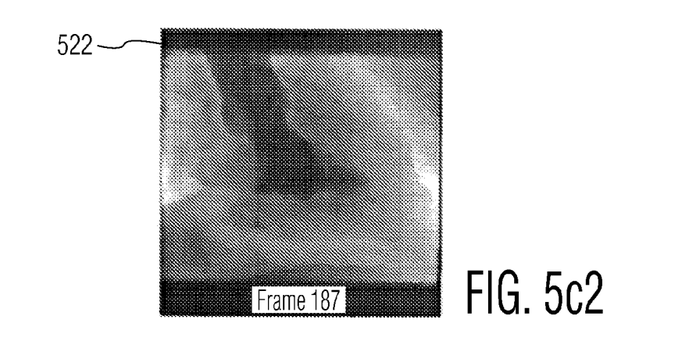

FIG. 4 illustrates a probability density function plotted against frame number N of a left ventricular angiogram. System 10 (FIG. 1) employs prior domain extra-systolic phenomenon knowledge in an ED and ES image retrieval system by advantageously integrating the prior domain information into a probability density function. In FIG. 4, probability density is plotted against frame number, where N is a total number of image frames in a left ventricular angiogram image sequence, $P_0$ is the image frame indicating the point in the image sequence when contrast agent is injected into left ventricle. The cardiac cycle around $P_0$ is the place where the extra-systolic phenomenon may occur. System 10 estimates the $P_0$ location as discussed later. In order to avoid any selection inside the extra-systolic cardiac cycle section, system 10 employs a delayed starting point $P_1$ as the starting point of an ED and ES image retrieval search range. The distance $P_0 P_1$ is a predefined constant, $P_3$ is a cutoff point used by system 10 to avoid ED and ES image selection from the end of an image sequence, where contrast agent fades away and a left ventricle area does not have sufficient image contrast. The length $P_3 N$ is an empirical number proportional to both total frame number N and image sequence frame rate $f_r$. $P_2$ is a middle point between $P_1$ and $P_3$. System 10 represents prior density of domain knowledge as, $$p_0(t) = \begin{cases} \frac{1}{\sqrt{2\pi}\sigma_P} \exp\left\{-\frac{(t-P_2)^2}{2\sigma_P^2}\right\} & \text{if } P_1 \le t \le P_3; \\ 0 & \text{otherwise} \end{cases} \quad (12)$$

where $\sigma_p$ is a variance constant.

System 10 image data processor 19 integrates image information, ECG signal data and prior domain knowledge for robust ED and ES image retrieval or identifying a substantially optimal ED image number $n_{ED}$ using cost function, $$n_{ED} = \arg\max_t \{f(t) \cdot E[p(x_{1:t} | z^h_{1:t}, z^s_{1:t})] \cdot p_0(t)\} \quad (13)$$

where $f(t)$ is an ED distribution density derived using ECG signal data, $p(x_{1:t}|z^h_{1:t}; z^s_{1:t})$ is a joint posterior density derived by image analysis, and $p_0(t)$ is a prior density derived from the domain information. The function assumes that the image data, ECG signal data and prior domain information are substantially independent.

In response to image data processor 19 identifying a substantially optimal ED image, processor 19 initiates identification of a substantially optimal ES image. Clinical protocol indicates that the ES image is likely to be within the same cardiac cycle as the identified optimal ED frame. Accurate determination of cardiac cycle length by computing the average distance between two consecutive ED images indicated by an ECG signal is difficult because of false positive and false negative detection of R-waves. The normal heart rate of a human being is between 50 beat per minute (bpm) to 120 bpm. Considering the abnormal cases that are often involved in left ventricular analysis, it may be assumed that heart rate is in a range of 40 to 150 bmp. So, one beat lasts 0.4 to 1.5 seconds. With the frame rate $f_r$, the range of a human possible cardiac length in terms of frame number [cMin;cMax], is cMin=0.4 $f_r$, cMax=1.5 $f_r$. These two numbers indicate a reasonable ES image search range which covers a substantial portion of the left ventricular angiogram image sequence data. In case, the range is invalid, system 10 prompts a user (e.g., physician) to perform a manual image inspection to identify an ES image. Image data processor 19 initiates a search of an angiogram image sequence for an optimal ES image comprising the first ES image within a range of cMin to cMax seconds following an identified optimal ED image. Processor 19 finds an optimal ES image using the cost function, $$n_{ES} = \arg\max_t \{E[p(x_{1:t} | z^h_{1:t}, z^s_{1:t})] \cdot \hat{p}_0(t)\} \quad (14)$$

where $\hat{p}_0(t)$ is the density of the ES search region and is, $$\hat{p}_0(t) = \quad (15)$$
$$\begin{cases} \frac{1}{\sqrt{2\pi}\sigma_{ES}} \exp\left\{-\frac{(t-\mu_{ES})^2}{2\sigma_{ES}^2}\right\} & \text{if}(n_{ED}+c\text{Min}) \le t \le (n_{ED}+c\text{Max}); \\ 0 & \text{otherwise} \end{cases}$$

where $\sigma_{es}$ is a variance constant, and $\sigma_{es}=(c\text{Min}+c\text{Max})=2+n_{ED}$.

A sample of forty six left ventricular angiograms was acquired from four hospitals in both the United States and Germany. The angiogram data was obtained during interventional surgery in a 30 degree right anterior oblique view, including different patients suffering from one, two or diffuse cardiac diseases. The frame rate was from 12.5 frame per second (fps) to 30 fps. The average acquisition time was 7 to 10 seconds, with a corresponding total frame number of 85 to 300 frames, covering 5 to 10 cardiac cycles. The image resolutions were also different. Some frames being of 512×512 resolution with an 8-bit pixel depth and some with 1024× 1024 resolution with a 12-bit pixel depth. The image data was normalized to a 512×512 resolution with an 8-bit pixel depth during an image preprocessing step and manual inspection was performed on the image sequences to identify the desired optimal ED and ES images.

FIG. 5 shows data analysis graphs and associated corresponding ED and ES images showing data derived from the sample forty six left ventricular angiograms. Graph 502 shows a cost function plotted against frame number N indicating optimal ED and ES images at frames 148 and 157 presented in images 510 and 512, respectively. Similarly, graph 504 shows the cost function plotted against frame number N indicating optimal ED and ES images at frames 176 and 187 presented in images 520 and 522, respectively. Image data processor 19 calculates cost function data comprising, curve 530 in graph 502 using a histogram-based observation likelihood function and curve 532 in graph 502 using a scene-based observation likelihood function. Image data processor 19 calculates cost function data comprising, curve 540 in graph 504 using a histogram-based observation likelihood function and curve 542 in graph 504 using a scene-based observation likelihood function. The dashed vertical lines e.g., lines 546 and 548 indicate ED image candidates indicated by the ECG signal and horizontal lines 550 and 552 comprise averages of curves 530 and 540. The first intersection of horizontal lines 550 and 552 with curves 530 and 540 respectively indicate the time when contrast agent was injected into a left ventricle. Labels 560 and 562 of graph 502 indicate location of optimal ED an ES image frames in a first angiogram image sequence. Labels 564 and 566 of graph 504 indicate location of optimal ED an ES image frames in a second angiogram image sequence.

Figure 6A:
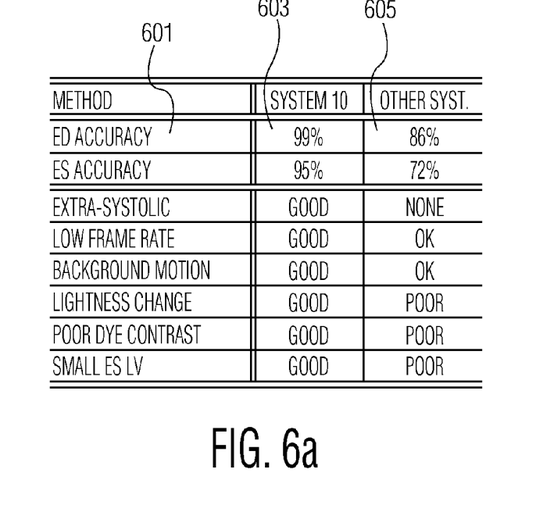
FIG. 6 shows Table 1 and Table 2 presenting comparison data between a system according to invention principles and another system.
Figure 6B:
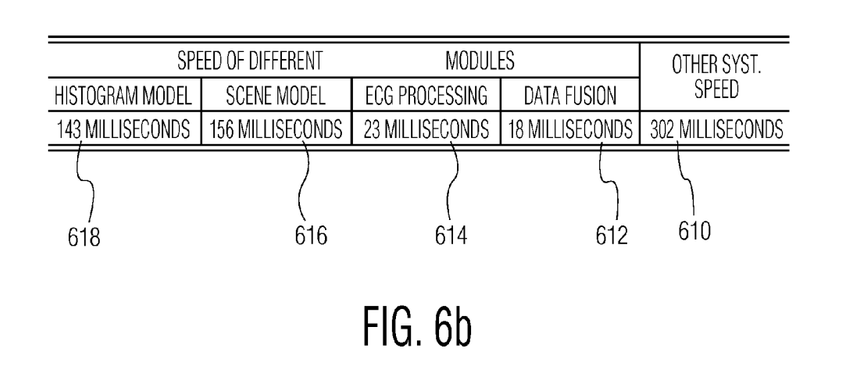

FIG. 6 shows Table 1 and Table 2 presenting comparison data between system 10 and a known system in automatic identification of ED and ES images in an angiogram. Table 1 shows comparison results characteristics identified in column 601 for system 10 in column 603 and for a known system in column 605. Specifically, columns 603 and 605 show ED accuracy, ES accuracy, Extra-systolic image identification capability, low frame rate performance, background motion performance, lightness change performance, poor contrast agent image contrast performance and small ES left ventricle performance. As can be seen by the four qualitative levels "Good", "OK", "Poor", and "None", system 10 ED and ES image automatic identification performance is substantially better than the known system in processing image sequences with poor image quality. In one exemplary embodiment, image data processor 19 is implemented in C++ using an OpenCV library on a laptop computer with Intel 2.33 Ghz Processor and 2 G RAM. Without code optimization, the average speed is 250 to 410 milliseconds for processing image sequences with 85 to 300 frames. System 10 employs additional computational resources for scene-based image feature extraction, ECG-based R-wave detection, and data combination, but saves resources and time on adaptive background modeling. Table 2 illustrates an average comparison of computational resource usage between different modules of system 10 and the known system. Specifically, the known system processing takes 302 ms (610) whereas in corresponding processing, image data processor 19 employs 143 ms (618) in histogram-based likelihood model processing, 156 ms (616) in scene-based likelihood model processing, 23 ms (614) in ECG signal processing and 18 ms (612) in data combination processing.

Figure 7:
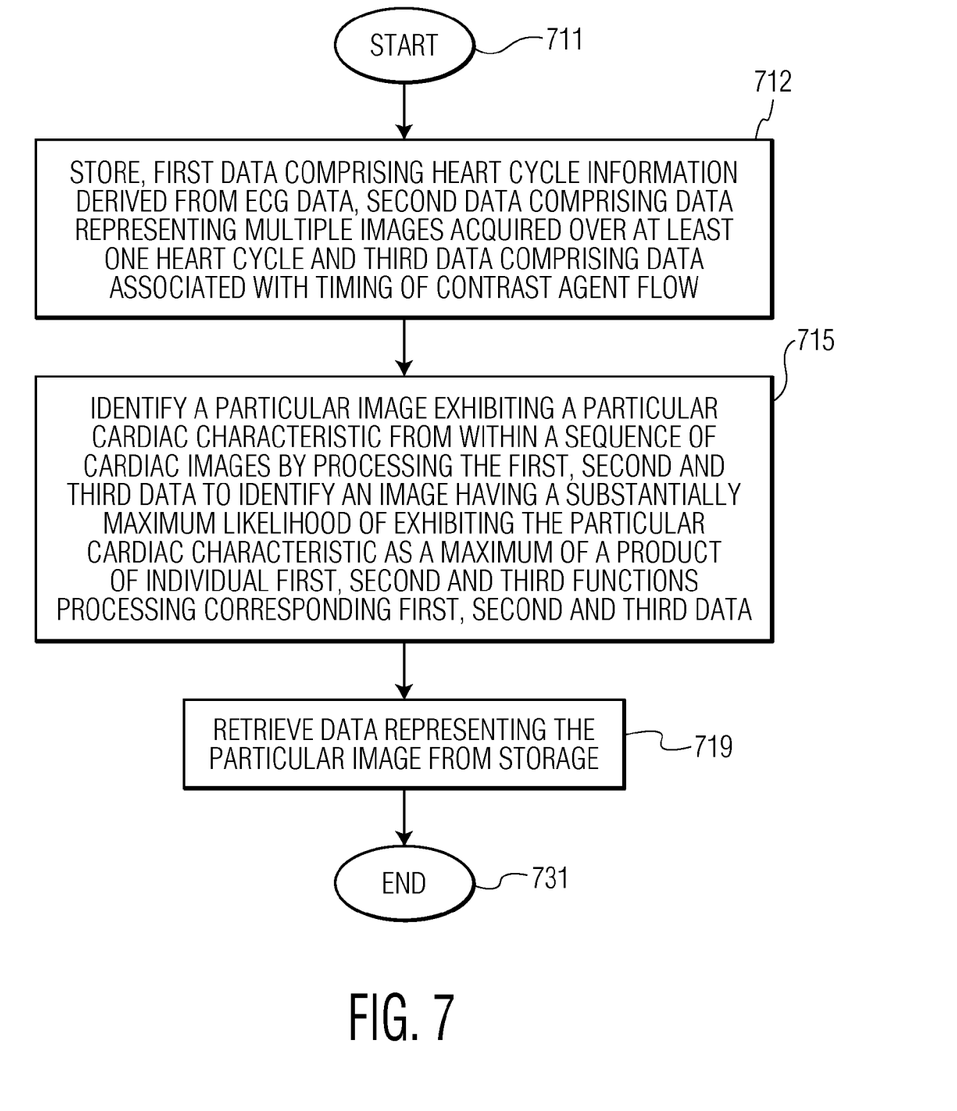
FIG. 7 shows a flowchart of a process used by a system for identifying a particular image associated with a particular cardiac characteristic, according to invention principles.

FIG. 7 shows a flowchart of a process used by system 10 for identifying a particular image associated with a particular cardiac characteristic from within a sequence of cardiac images including image noise artifacts and obtained over a heart beat cycle. The particular cardiac characteristic is an end-diastolic (ED) phase of a heart and image data processor 19 also identifies a particular image exhibiting a particular cardiac characteristic comprising an end-systolic (ES) phase of a heart. Image data processor 19 identifies a particular image exhibiting an end-systolic (ES) phase of a heart within a search range determined based on a predetermined heart beat range. In step 712 following the start at step 711, system 10 stores in at least one repository 17 (FIG. 1), first data comprising heart cycle information derived from ECG data, second data comprising data representing multiple images acquired over at least one heart cycle and third data comprising data associated with timing of contrast agent flow.

In step 715, image data processor 19 identifies a particular image exhibiting a particular cardiac characteristic from within a sequence of cardiac images by processing the first, second and third data to identify an image having a substantially maximum likelihood of exhibiting the particular cardiac characteristic as a maximum of a product of individual first, second and third functions processing corresponding first, second and third data. Image data processor 19 determines the substantially maximum likelihood of exhibiting the particular cardiac characteristic as a maximum of a product of individual first, second and third functions processing corresponding first, second and third data. The maximum of the product of the individual first, second and third functions represents a cost function integrating the individual first, second and third functions. The function integrating the individual first, second and third functions determines an estimation of an optimal image number $n_{ED}$ by the following cost function, $$n_{ED} = \operatorname*{argmax}_{t}\{f(t) \cdot E[p(x_{1:t} | z^h_{1:t}, z^s_{1:t})] \cdot p_0(t)\}$$

where, f(t) is an image data distribution density derived from the first data, $p(x_{1:t}|z^h_{1:t}; z^s_{1:t})$ is a joint posterior density derived by image analysis of the second data, and $p_0(t)$ is a prior density derived from the third data. Image data processor 19 identifies an image frame number of the particular image from a set of sequential frame numbers associated with multiple corresponding images acquired over at least one heart cycle. In step 719, storage processor 36 retrieves data representing the particular image from storage. The process of FIG. 7 terminates at step 731.

The systems and processes of FIGS. 1-7 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 provides real-time intelligent automatic ED and ES image identification in X-ray left ventricular angiograms using Bayesian probability propagation and data combination integrating prior domain knowledge as well as ECG and image information. Further, the systems and processes may, in alternative embodiments, be located on one or more (e.g., distributed) processing devices. Any of the functions and steps provided in FIGS. 1-7 may be implemented in hardware, software or a combination of both.

What is claimed is:

1. A system for identifying a particular image associated with a particular cardiac characteristic from within a sequence of cardiac images including image noise artifacts and obtained over a heart beat cycle, comprising: at least one processing device including, at least one non-transitory computer readable storage medium including, first data comprising heart cycle information derived from ECG data, second data comprising data representing a plurality of images acquired over at least one heart cycle and third data comprising data associated with timing of substantially X-ray opaque contrast agent flow, which enhancing visualization of heart ventricle variation and enabling identification of a heart image acquired during a particular cardiac cycle exhibiting substantially optimum image contrast due to the X-ray opaque contrast agent flow; an image data processor for automatically identifying a particular image exhibiting a particular cardiac characteristic from within a sequence of cardiac images by processing the first, second and third data to identify an image having a substantially maximum likelihood of exhibiting said particular cardiac characteristic at a particular cardiac cycle phase and with substantially optimum image contrast; and a storage processor for retrieving data representing said particular image from a storage device.

2. A system according to claim 1, wherein said image data processor determines said substantially maximum likelihood of exhibiting said particular cardiac characteristic as a maximum of a product of individual first, second and third functions processing corresponding to the first, second and third data.

3. A system according to claim 2, wherein
said maximum of said product of said individual first, second and third functions represents a cost function integrating said individual first, second and third functions.

4. A system according to claim 3, wherein said cost function integrating said individual first, second and third functions determines an estimation of an optimal image number $n_{ED}$ by the following cost function, $n_{ED}=\operatorname{argmax}_{t}\{f(t)*E[p(x_{1:t}|z^h_{1:t}, z^s_{1:t})]*p_0(t)\}$ where, f(t) is an image data distribution density derived from the first data, $p(x_{1:t}|z^h_{1:t}, z^s_{1:t})$ is a joint posterior density derived by image analysis of the second data, and $p_0(t)$ is a prior density derived from the third data.

5. A system according to claim 1, wherein
said particular cardiac characteristic is an end-diastolic (ED) phase of a heart.

6. A system according to claim 5, wherein
said image data processor also identifies a particular image exhibiting a particular cardiac characteristic comprising an end-systolic (ES) phase of a heart.

7. A system according to claim 5, wherein
said image data processor identifies a particular image exhibiting an end-systolic (ES) phase of a heart within a search range determined based on a predetermined heart beat range.

8. A system according to claim 1, wherein
said particular cardiac characteristic is an end-systolic (ES) phase of a heart.

9. A system according to claim 1, wherein
said image data processor identifies an image frame number of said particular image from a set of sequential frame numbers associated with a plurality of corresponding images acquired over at least one heart cycle.

10. A system for identifying a particular image associated with a particular cardiac characteristic from within a sequence of cardiac images including image noise artifacts and obtained over a heart beat cycle, comprising: at least one processing device including, at least one non-transitory computer readable storage medium including, first data comprising heart cycle information derived from ECG data, second data comprising data representing a plurality of images acquired over at least one heart cycle and third data comprising data associated with timing of substantially X-ray opaque contrast agent flow, which enhancing visualization of heart ventricle variation and enabling identification of a heart image acquired during a particular cardiac cycle exhibiting substantially optimum image contrast due to the X-ray opaque contrast agent flow; an image data processor for automatically, identifying a particular image exhibiting a particular cardiac characteristic from within a sequence of cardiac images by processing the first, second and third data to identify an image having a substantially maximum likelihood of exhibiting said particular cardiac characteristic at a particular cardiac cycle, phase and with substantially optimum image contrast as a maximum of a product of individual first, second and third functions processing corresponding to the first, second and third data; and a storage processor for retrieving data representing said particular image from a storage device.

11. A method for identifying a particular image associated with a particular cardiac characteristic from within a sequence of cardiac images including image noise artifacts and obtained over a heart beat cycle, comprising the activities of: employing at least one processing device for, storing, first data comprising heart cycle information derived from ECG data, second data comprising data representing a plurality of images acquired over at least one heart cycle and third data comprising data associated with timing of substantially X-ray opaque contrast agent flow, which enhancing visualization of heart ventricle variation and enabling identification of a heart image acquired during a particular cardiac cycle exhibiting substantially optimum image contrast due to the X-ray opaque contrast agent flow; automatically identifying a particular image exhibiting a particular cardiac characteristic from within a sequence of cardiac images by processing the first, second and third data to identify an image having a substantially maximum likelihood of exhibiting said particular cardiac characteristic at a particular cardiac cycle phase and with substantially optimum image contrast; and retrieving data representing said particular image from a storage device.

* * * * *